US012728000B2

(12) United States Patent
Giese et al.

(10) Patent No.: US 12,728,000 B2
(45) Date of Patent: Sep. 8, 2026

(54) DEVICES, SYSTEMS, AND METHODS FOR POSITIONING AN ANCHOR FOR AN ARTIFICIAL CHORDAE TENDINEAE

(71) Applicant: BOSTON SCIENTIFIC SCIMED, INC., Maple Grove, MN (US)

(72) Inventors: Troy Anthony Giese, Blaine, MN (US); Joel T. Eggert, Plymouth, MN (US); Christopher J. Koudela, New London, MN (US); Larry Michael Killeen, Elk River, MN (US); Nicholas Barron, Columbia Heights, MN (US); Matthew P. Jones, Shoreview, MN (US); Kristen Elizabeth Ott, White Bear Lake, MN (US); James K. Cawthra, Jr., Ramsey, MN (US); Charanjit S. Rihal, Rochester, MN (US); Mackram F. Eleid, Rochester, MN (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 919 days.

(21) Appl. No.: 17/899,486

(22) Filed: Aug. 30, 2022

(65) Prior Publication Data

US 2023/0190470 A1 Jun. 22, 2023

Related U.S. Application Data

(60) Provisional application No. 63/291,758, filed on Dec. 20, 2021.

(51) Int. Cl.
*A61F 2/24* (2006.01)

(52) U.S. Cl.
CPC .......... *A61F 2/2466* (2013.01); *A61F 2/2457* (2013.01); *A61F 2250/0096* (2013.01)

(58) Field of Classification Search
CPC ........ A61F 2/24; A61F 2/2466; A61F 2/2457; A61F 2250/0096
See application file for complete search history.

(56) References Cited

U.S. PATENT DOCUMENTS 5,702,397 A 12/1997 Goble et al.
7,736,388 B2 6/2010 Goldfarb et al.
(Continued)

FOREIGN PATENT DOCUMENTS

EP 3104772 B1 3/2019
JP 2005537067 A 12/2005
(Continued)

OTHER PUBLICATIONS

International Search Report and Written Opinion for International Application No. PCT/US2022/042085, date of mailing Dec. 5, 2022, 11 pages.

(Continued)

*Primary Examiner* — Vi X Nguyen
(74) *Attorney, Agent, or Firm* — Seager, Tufte & Wickhem, LLP

(57) ABSTRACT

Implantable devices formed of materials which are not readily imageable, and which may shift from a delivery configuration to a deployment configuration upon deployment, are delivered and deployed with a deployment/delivery device having sensors generating a signal indicating contact of the delivery/deployment device with tissue to guarantee purchase of the implantable device with tissue upon deployment. The implantable device may be a tissue anchor with talons which shift from a delivery configuration to a deployed configuration. The sensors may be positioned along a distal end of the delivery/deployment device to indicate purchase of the device with tissue, to ensure purchase of the talons with tissue upon deployment. The sensors may include at least three sensors, which may be spaced (Continued)

apart from one another, to indicate full contact of the distal end of the delivery/deployment device with tissue. The sensors may optionally be aligned with the talons.

19 Claims, 3 Drawing Sheets

(56) References Cited

U.S. PATENT DOCUMENTS

| | | | |
|---|---|---|---|
| 8,252,050 B2 | 8/2012 | Maisano et al. | |
| 8,303,622 B2 | 11/2012 | Alkhatib | |
| 8,852,088 B2 | 10/2014 | Ransden et al. | |
| 9,572,667 B2 | 2/2017 | Solem | |
| 9,681,864 B1 | 6/2017 | Gammie et al. | |
| 10,136,993 B1 | 11/2018 | Metchik et al. | |
| 10,179,236 B2 | 1/2019 | Haasl et al. | |
| 10,478,629 B2 | 11/2019 | An et al. | |
| 10,945,718 B2 | 3/2021 | Hiorth et al. | |
| 2004/0088003 A1 | 5/2004 | Leung et al. | |
| 2004/0230280 A1 | 11/2004 | Cates et al. | |
| 2006/0207607 A1 | 9/2006 | Hirotsuka et al. | |
| 2006/0276890 A1 | 12/2006 | Solem et al. | |
| 2007/0080188 A1* | 4/2007 | Spence | A61F 2/2445 623/2.11 |
| 2007/0118151 A1 | 5/2007 | Davidson | |
| 2008/0051863 A1 | 2/2008 | Schneider et al. | |
| 2008/0195126 A1 | 8/2008 | Solem | |
| 2009/0105729 A1 | 4/2009 | Zentgraf | |
| 2011/0060407 A1 | 3/2011 | Ketai et al. | |
| 2011/0301699 A1 | 12/2011 | Saadat | |
| 2012/0130492 A1 | 5/2012 | Eggli et al. | |
| 2012/0172892 A1 | 7/2012 | Grubac et al. | |
| 2013/0096611 A1 | 4/2013 | Sullivan | |
| 2013/0110230 A1 | 5/2013 | Solem | |
| 2015/0223704 A1 | 8/2015 | Haverkost et al. | |
| 2015/0250590 A1 | 9/2015 | Gries et al. | |
| 2017/0245993 A1 | 8/2017 | Gross et al. | |
| 2017/0252032 A1 | 9/2017 | Hiorth et al. | |
| 2018/0185153 A1 | 7/2018 | Bishop et al. | |
| 2018/0250133 A1 | 9/2018 | Reich et al. | |
| 2018/0296327 A1 | 10/2018 | Dixon et al. | |
| 2018/0303614 A1 | 10/2018 | Schaffner et al. | |
| 2019/0314634 A1 | 10/2019 | Deininger et al. | |
| 2019/0343634 A1 | 11/2019 | Garvin et al. | |
| 2020/0163768 A1 | 5/2020 | Apkarian et al. | |
| 2020/0261699 A1 | 8/2020 | Rizq et al. | |
| 2021/0000597 A1 | 1/2021 | Shuey et al. | |
| 2021/0000598 A1* | 1/2021 | Shuey | A61B 17/0401 |
| 2021/0000599 A1 | 1/2021 | Shuey et al. | |
| 2021/0007847 A1 | 1/2021 | Eggert et al. | |
| 2022/0015904 A1 | 1/2022 | Hiorth et al. | |
| 2022/0022863 A1 | 1/2022 | Hiorth et al. | |
| 2022/0096235 A1 | 3/2022 | Giese et al. | |

FOREIGN PATENT DOCUMENTS

| | | |
|---|---|---|
| WO | 2004019826 A1 | 3/2004 |
| WO | 2015193728 A2 | 12/2015 |
| WO | 2020123719 A1 | 6/2020 |
| WO | 2021080782 A1 | 4/2021 |

OTHER PUBLICATIONS

International Search Report and Written Opinion for the International Application No. PCT/US2020/040678, mailed Oct. 16, 2020, 10 pages.

International Search Report and Written Opinion for the International Patent Application No. PCT/US2020/040672, mailed Oct. 16, 2020.

"Fish Fighter® Kwik-Pull™ Anchor Retriever" Fish Fighter Products, 6 pages, URL: https://fishfighterproducts.com/shop/fish-fighter-kwik-pull-anchor-retriever/ Retrieved Aug. 29, 2020.

"Knotless SutureTak® Anchor" Arthrex, 2 pages, 1 page, URL: https://www.arthrex.com/resources/animation/2d7_OmxWw0edpgFLMMbz5A/knotless-suturetak-anchor. Retrieved Aug. 29, 2020.

"Shoulder Labral Repair with Knotless SutureTak® Anchor" Arthrex, retrieved Aug. 29, 2020, URL: https://www.arthrex.com/resources/animation/9cpCPTZLCEGvYQFMdIKwxg/shoulder-labral-repair-with-knotless-suturetak-anchor 7 pages. Retrieved Aug. 29, 2020.

"Knotless SutureTak Anchor Instability Repair" Arthrex, 6 pages, 2018.

APS—Annapolis Performance Sailing., "Ronstan Constrictor Rope Clutch| Expert Review"—YouTube, 3 pages. Retrieved Oct. 9, 2020.

International Search Report and Written Opinion for the International Patent Application No. PCT/US2021/051722, mailed Jan. 7, 2022, 10 pages.

* cited by examiner

DEVICES, SYSTEMS, AND METHODS FOR POSITIONING AN ANCHOR FOR AN ARTIFICIAL CHORDAE TENDINEAE

CROSS-REFERENCE TO RELATED APPLICATIONS

This application claims the benefit of priority of U.S. Provisional Application No. 63/291,758, filed Dec. 20, 2021, the entire disclosure of which is hereby incorporated by reference herein for all purposes.

FIELD

The present disclosure relates generally to the field of implantable medical devices. In particular, the present disclosure relates to medical devices, systems, and methods for delivering and deploying implantable devices. More particularly, the present disclosure relates to medical devices, systems, and methods for delivering and deploying an anchor to ensure engagement with and into cardiac tissue.

BACKGROUND

Devices, systems, and methods for delivering and deploying implantable devices with minimally invasive techniques, such as transluminally, are desirable for avoiding more complex and invasive open surgery procedures. For instance, various techniques for cardiac surgery, such as repairing or replacing artificial chordae tendineae, including anchoring the artificial chordae tendineae to heart tissue, have been developed using transcatheter techniques without requiring open heart surgery. Transcatheter or otherwise noninvasive procedures generally require simultaneous visualization of both the targeted anatomy and the implant tools (delivery and deployment tools, as well as the implant itself). Unfortunately, current visualization tools are incapable of identifying both tissue as well as inorganic materials from which implant tools are made (e.g., metals, polymers, ceramics, etc.). Ultrasound easily identifies tissue, but struggles with many foreign materials, especially metallic components commonly implemented in medical devices and associated mechanisms and systems. As such, the devices and systems tend to cast shadows with fluoroscopy, obstructing the view of targeted tissues and often the devices and mechanisms as well. Fluoroscopy is well suited for viewing dense materials, but is generally unsuitable for visualizing many soft tissues (such as heart leaflets).

Solutions for verifying accurate positioning of a device for delivering and deploying an implant, such as an artificial chordae tendineae anchor with respect to heart tissue, and/or proper implantation of such anchor would be welcome.

SUMMARY

This summary of the disclosure is given to aid understanding, and one of skill in the art will understand that each of the various aspects and features of the disclosure may advantageously be used separately in some instances, or in combination with other aspects and features of the disclosure in other instances. No limitation as to the scope of the claimed subject matter is intended by either the inclusion or non-inclusion of elements, components, or the like in this summary.

In accordance with various principles of the present disclosure, a delivery device configured to deliver an implantable device includes three or more sensors positioned along a distal end of the delivery device and configured to generate a signal when the distal end of the delivery device is in contact with tissue to ensure purchase of tissue by the implantable device upon deployment.

In some embodiments, the three or more sensors are positioned spaced apart along a periphery of a distal end of the delivery device. In some embodiments, the three or more sensors are equidistantly spaced apart from one another.

In some embodiments, the delivery device is an anchor garage configured to deliver a tissue anchor to a deployment site, the tissue anchor having two or more talons shiftable from a delivery configuration to a deployment configuration. In some embodiments, the three or more sensors include at least one sensor associated with each talon of the tissue anchor delivered by the anchor garage. In some embodiments, the anchor garage has a blunt distal end along which the three or more sensors are positioned.

In some embodiments, the three or more sensors include contact sensors.

In some embodiments, the delivery and deployment device further includes a delivery shaft through which lead wires extend from the three or more sensors.

In accordance with various principles of the present disclosure, a system for delivering and deploying an implantable device to a deployment site in a body includes an implantable device; a delivery device configured to deliver the implantable device to the deployment site, and three or more sensors positioned along a distal end of the delivery device and configured to generate a signal when the distal end of the delivery device is in contact with tissue to ensure purchase of tissue by the implantable device upon deployment without the need for imaging.

In some embodiments, the three or more sensors are positioned spaced apart along a periphery of a distal end of the delivery device.

In some embodiments, the implantable device is a tissue anchor; and the delivery device is an anchor garage configured to deliver the tissue anchor to a deployment site. In some embodiments, the tissue anchor is clocked with respect to the anchor garage. In some embodiments, the tissue anchor has two or more talons shiftable from a delivery configuration to a deployment configuration; and the three or more sensors include at least one sensor associated with a talon of the tissue anchor. In some embodiments, the anchor garage includes a projection extending longitudinally along a portion thereof engaging a groove extending longitudinally along a portion of the tissue anchor to clock the tissue anchor with respect to the anchor garage. Lead wires from the three or more sensors extend within the projection along the anchor garage to a device generating a signal indicating contact of the three or more sensors with tissue. In some embodiments, the tissue anchor is clocked with respect to the anchor garage to align at least one of the talons of the tissue anchor with a sensor of the three or more sensors. In some embodiments, the system further includes an artificial chordae tendineae tensioning and locking device associated with the tissue anchor, and the tissue anchor is clocked with respect to the anchor garage to align an artificial chordae tendineae associated with the artificial chordae tendineae tensioning and locking device with a groove in the anchor garage.

In accordance with various principles of the present disclosure, a method of deliver and deploying an implantable device includes delivering a delivery and deployment device transluminally to a deployment site within a body; and contacting three or more sensors on a distal end of the delivery and deployment device with tissue at the delivery site to generate a signal indicative of a position of the delivery and deployment device ensuring purchase of the implantable device with tissue at the deployment site.

In some embodiments, the three or more sensors are positioned spaced apart along a distal end of the delivery and deployment device, and the method further includes deploying the implantable device when three of the three or more sensors generate a signal indicating contact with tissue. In some embodiments, the deployment site is cardiac tissue and the implantable device is a tissue anchor, the method further including deploying the tissue anchor into cardiac tissue when all three of the three or more sensors generate a signal indicating contact of a distal end of the delivery and deployment device with tissue at the deployment site and without imaging the implantable device or the deployment site.

These and other features and advantages of the present disclosure, will be readily apparent from the following detailed description, the scope of the claimed invention being set out in the appended claims. While the following disclosure is presented in terms of aspects or embodiments, it should be appreciated that individual aspects can be claimed separately or in combination with aspects and features of that embodiment or any other embodiment.

BRIEF DESCRIPTION OF THE DRAWINGS

Non-limiting embodiments of the present disclosure are described by way of example with reference to the accompanying drawings, which are schematic and not intended to be drawn to scale. The accompanying drawings are provided for purposes of illustration only, and the dimensions, positions, order, and relative sizes reflected in the figures in the drawings may vary. For example, devices may be enlarged so that detail is discernable, but is intended to be scaled down in relation to, e.g., fit within a working channel of a delivery catheter or endoscope. In the figures, identical or nearly identical or equivalent elements are typically represented by the same reference characters, and similar elements are typically designated with similar reference numbers differing in increments of 100, with redundant description omitted. For purposes of clarity and simplicity, not every element is labeled in every figure, nor is every element of each embodiment shown where illustration is not necessary to allow those of ordinary skill in the art to understand the disclosure.

The detailed description will be better understood in conjunction with the accompanying drawings, wherein like reference characters represent like elements, as follows.

DETAILED DESCRIPTION

Figure 1:
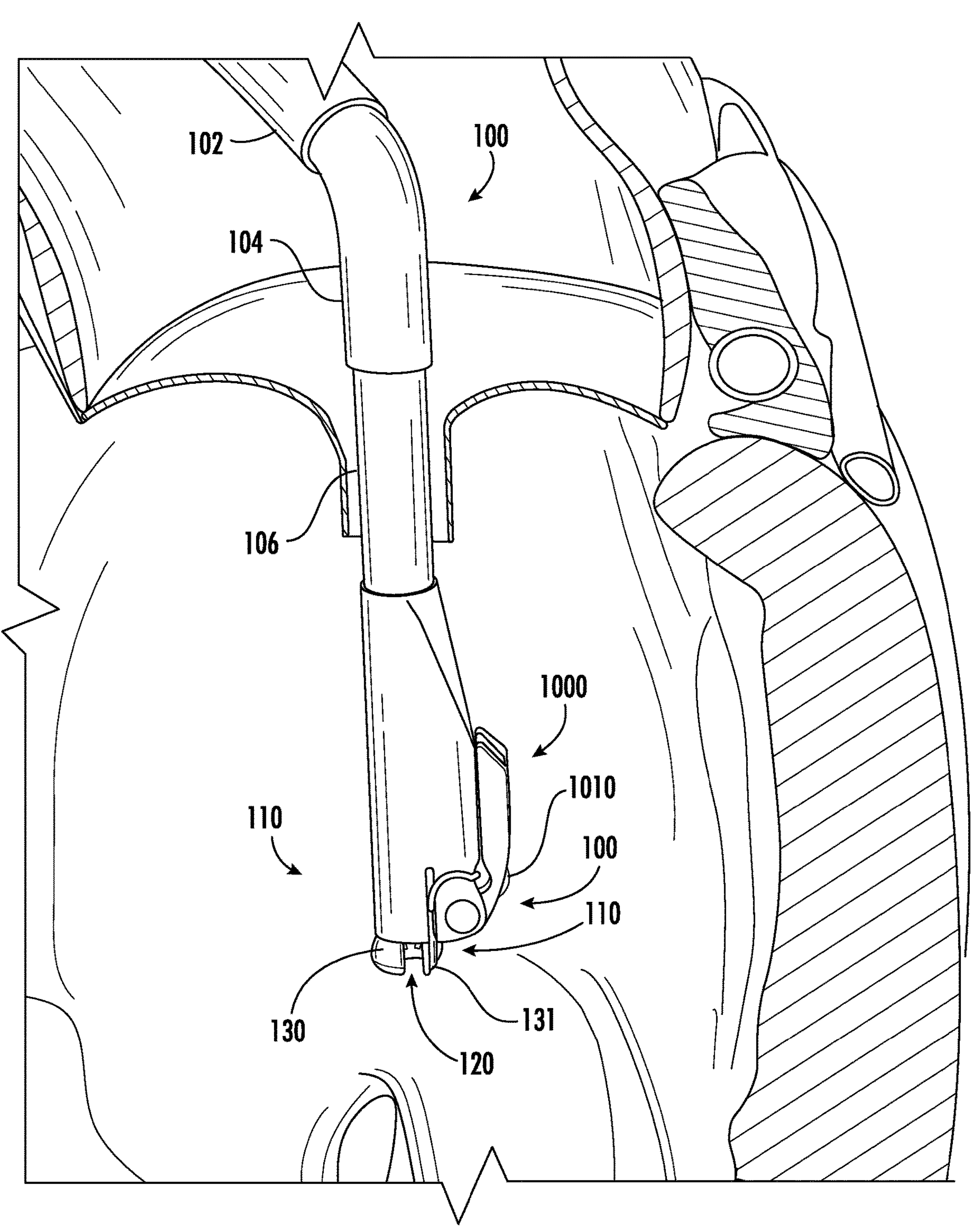
FIG. 1 illustrates a perspective view of an example of an embodiment of an anchor delivery and deployment device and system formed in accordance with various principles of the present disclosure shown in a schematic representation of a heart for deployment of an anchor in cardiac tissue.

The following detailed description should be read with reference to the drawings, which depict illustrative embodiments. It is to be understood that the disclosure is not limited to the particular embodiments described, as such may vary. All apparatuses and systems and methods discussed herein are examples of apparatuses and/or systems and/or methods implemented in accordance with one or more principles of this disclosure. Each example of an embodiment is provided by way of explanation and is not the only way to implement these principles but are merely examples. Thus, references to elements or structures or features in the drawings must be appreciated as references to examples of embodiments of the disclosure, and should not be understood as limiting the disclosure to the specific elements, structures, or features illustrated. Other examples of manners of implementing the disclosed principles will occur to a person of ordinary skill in the art upon reading this disclosure. In fact, it will be apparent to those skilled in the art that various modifications and variations can be made in the present disclosure without departing from the scope or spirit of the present subject matter. For instance, features illustrated or described as part of one embodiment can be used with another embodiment to yield a still further embodiment. Thus, it is intended that the present subject matter covers such modifications and variations as come within the scope of the appended claims and their equivalents.

It will be appreciated that the present disclosure is set forth in various levels of detail in this application. In certain instances, details that are not necessary for one of ordinary skill in the art to understand the disclosure, or that render other details difficult to perceive may have been omitted. The terminology used herein is for the purpose of describing particular embodiments only, and is not intended to be limiting beyond the scope of the appended claims. Unless defined otherwise, technical terms used herein are to be understood as commonly understood by one of ordinary skill in the art to which the disclosure belongs. All of the devices and/or methods disclosed and claimed herein can be made and executed without undue experimentation in light of the present disclosure.

As used herein, “proximal” refers to the direction or location closest to the user (medical professional or clinician or technician or operator or physician, etc., such terms being used interchangeably herein without intent to limit, and including automated controller systems or otherwise), etc., such as when using a device (e.g., introducing the device into a patient, or during implantation, positioning, or delivery), and/or closest to a delivery device, and “distal” refers to the direction or location furthest from the user, such as when using the device (e.g., introducing the device into a patient, or during implantation, positioning, or delivery), and/or closest to a delivery device. “Longitudinal” means extending along the longer or larger dimension of an element. “Central” means at least generally bisecting a center point and/or generally equidistant from a periphery or boundary, and a “central axis” means, with respect to an opening, a line that at least generally bisects a center point of the opening, extending longitudinally along the length of the opening when the opening comprises, for example, a tubular element, a channel, a cavity, or a bore.

Various devices and systems delivered transluminally within a patient’s body include components formed of a metal or other material which is not readily visible or visualized or otherwise discernible with typical or current imaging systems (e.g., fluoroscopy or ultrasound imaging) for imaging body tissue. Tools and systems for visualizing/imaging tissue generally do not provide sufficiently clear visualization of metal or polymeric systems or devices delivered to such tissue. In accordance with various principles of the present disclosure, devices, systems, and methods described herein facilitate manipulation of devices and systems with respect to body tissue without visualizing or imaging the device or system (such as with tools or systems used to visualize or image the body tissue). More particularly, various principles of the present disclosure facilitate fixation of one or more devices with respect to tissue, such as to cardiac tissue (e.g., papillary muscle tissue). Even more particularly, various principles of the present disclosure facilitate fixation of an anchor device to tissue. It will be appreciated that the term anchor device is used for the sake of convenience and may be used interchangeably herein with terms such as anchor, anchor element, anchor mechanism, anchor component, anchoring element, anchoring device, anchoring mechanism, anchoring component, and the like, such terms being known in the art to represent structures configured to be held in place and optionally also to hold another object in place. It will further be appreciated that various terms (in various grammatical forms) may be used interchangeably herein to refer to the attachment of an anchor to tissue, such as attach, anchor, implant, affix, secure, couple, engage, hold, retain, embed, purchase etc., without intent to limit. In accordance with various principles of the present disclosure, sensors, such as contact sensors, are associated with the implantable device and/or delivery and deployment device and/or system to provide information not readily discernible with typical or current imaging technology so that the delivery/deployment device and/or the implantable device need not be imaged or visualized to determine the relationship (e.g., spatial, degree of contact, etc.) provided on at least a portion of the delivery and deployment device to facilitate placement of a device with respect to tissue.

Devices, systems, and methods of the present disclosure may be used alone or together with other devices, systems, and methods to treat heart disease. For instance, principles of the present disclosure may be applied to procedures for repairing heart valves (e.g., to ensure proper functioning and closure of heart valves), such as repositioning, repairing, and/or replacing one or more heart valve leaflets and/or chordae tendineae. Examples of devices, systems, and methods with which embodiments of the present disclosure may be implemented include, but are not limited to, those described in U.S. Patent Application Publication US2021/0007847, titled Devices, Systems, And Methods For Clamping A Leaflet Of A Heart Valve, and published on Jan. 14, 2021; U.S. Patent Application Publication US2021/0000597, titled Devices, Systems, And Methods For Adjustably Tensioning An Artificial Chordae Tendineae Between A Leaflet And A Papillary Muscle Or Heart Wall, and published on Jan. 7, 2021; U.S. Patent Application Publication US2021/0000599, titled Devices, Systems, And Methods For Artificial Chordae Tendineae, and published on Jan. 7, 2021; U.S. Patent Application Publication US2021/0000598, titled Devices, Systems, And Methods For Anchoring An Artificial Chordae Tendineae To A Papillary Muscle Or Heart Wall, and published on Jan. 7, 2021; and U.S. Patent Application 63/085,390, filed on Sep. 30, 2020; U.S. Patent Application 63/239,467 filed Sep. 1, 2021; and U.S. Provisional Patent Application 63/239,469, filed Sep. 1, 2021, each of which is herein incorporated by reference in its entirety and for all purposes. It will be appreciated that devices and systems described herein may be used with devices or systems disclosed in the above-referenced applications incorporated herein, or may be used with other devices and systems.

Intravenous/transcatheter replacement of one or more artificial chordae tendineae involves attaching an artificial chordae tendineae, such as an expanded polytetrafluoroethylene (ePTFE) suture, to cardiac tissue, such as the ventricle wall/papillary muscle. Various methods of attaching the artificial chordae tendineae use an anchor device, such an anchor with one or more (and typically two or more, such as three or more, or even four or more) talons. An anchor used in accordance with various principles of the present disclosure may include a plurality of talons which are biased into a deployed configuration for engaging tissue, yet which may be positioned in a delivery configuration for delivery to tissue, such as within an anchor delivery and deployment device of an anchor delivery and deployment system. The delivery configuration may be a compact or compressed configuration, and the deployment configuration may be an open or expanded configuration (with an outer dimension greater than the outer dimension of the anchor when in a delivery configuration). If pushed against body tissue, the anchor talons may pierce and penetrate into the tissue and spread into a deployed configuration secured within the body tissue. The anchor (including the talons thereof) may be formed of an elastic and/or shape memory material, such as Nitinol, formed (e.g., by heat treating) into the desired open configuration and shaped to ensure secure connection of the anchor with the cardiac tissue. As such, the anchor talons are biased to substantially automatically open into the open configuration without external forces moving the anchor talons. It will be appreciated that terms such as open, expand, shift, move, transition, etc. (and various grammatical forms thereon) may be used interchangeably herein to refer to the movement of the anchor talons without intent to limit. An example of an artificial chordae tendineae anchor which may be used with devices, systems, and methods disclosed herein includes, without limitation, anchors as disclosed in above-referenced and incorporated-by-reference U.S. Provisional Patent Application 63/239,469, filed Sep. 1, 2021.

In general, it is desirable for the distal end of an anchoring device such as an artificial chordae tendineae anchor to properly and/or fully engage tissue with which the anchoring device is to engaged. For instance, if the artificial chordae tendineae anchor includes one or more talons, it is generally desirable for the distal end of the talons to engage the tissue in which the talon is to be embedded before deployment from the delivery and deployment device. It will be appreciated that terms such as deploy, eject, push, release, propel, expel, dispense, etc., (and various grammatical forms thereof) may be used interchangeably herein without intent to limit. In some embodiments, the anchor is deployed by being pushed from a delivery position with respect to the delivery deployment device (e.g., within a garage or other seat or delivery area on the delivery and deployment device) into the cardiac tissue. If a portion of the anchor, such as the talons, changes position or configuration upon deployment (e.g., the talons curve outwardly to securely engage within the tissue to hold the anchor in place), it may be particularly important for such portion to engage tissue before deployment. More particularly, engagement of such portion of the anchor with tissue before pushing the anchor into the cardiac tissue allows such portion to penetrate the tissue before changing position or configuration.

Because current visualization/imaging tools generally do not provide sufficiently clear visualization of both body tissue as well as devices such as anchors, it is generally difficult to ensure appropriate tissue contact along the distal end of an anchor, such as to visualize the anchor talons as well as the tissue entry points at which the anchor talons are to penetrate into the tissue. Lack of contact of the anchor with tissue typically will result in that portion of the anchor (e.g., a talon) not purchasing or penetrating the tissue. Moreover, it is generally desirable to locate the anchor at the proper tissue, such as muscle tissue rather than fat tissue, and/or at the proper position, such as in papillary tissue rather than in the apex of the heart, and/or orientation.

In accordance with various principles of the present disclosure, one or more sensors are associated with an implantable device, a delivery and deployment device, and/or a delivery and deployment system such as to convey information about the implantable device and a deployment site. The sensor may include an electrode (such as a conductive pad) and corresponding electronics. The information may include, without limitation, the degree of engagement of the delivery and deployment device with respect to tissue at the deployment site, the position of the implantable device relative to tissue at the deployment site, and/or further information about the device or system, etc. It will be appreciated that terms such as deployment site, treatment site, implantation site, etc. may be used interchangeably herein without intent to limit. It will be appreciated that references herein to delivery and/or deployment are intended to include delivery, or deployment, or both. It will further be appreciated that deployment may include securing in addition to placing of a device. The delivery/deployment device may be configured to hold and/or carry the implantable device for delivery to the deployment site, and/or to facilitate deployment of the implantable device into tissue. For instance, the delivery/deployment device may be configured to manipulate the implantable device for positioning and deploying (e.g., securing, implanting, anchoring, etc.) with respect to tissue at the deployment site. It will be appreciated that terms such as manipulate (and other grammatical forms thereof) may be used interchangeably herein with such terms (and other grammatical forms thereof) as actuate, control, maneuver, move, operate, shift, transition, drive, advance, retract, rotate, translate, etc., without intent to limit.

In some embodiments, the one or more sensors are contact sensors. For instance, the one or more sensors may provide a direct indication of the level of engagement of at least the delivery and deployment device with tissue in which the anchor is to be deployed. The one or more sensors relay a signal to the medical professionals using the system to implant the anchor (e.g., a surgical team) when in contact with tissue or at least when the delivery and deployment device sufficiently contacts tissue to ensure proper deployment of the anchor. Such information is conveyed to the medical professionals (e.g., surgical team, including any automated system being utilized) in any of a variety of manners (e.g., visual or audible indication, such as on a delivery system or separate associated device) to facilitate placement, implantation, etc., of the anchor device. For instance, such information may be used to guide placement of the anchor and the deployment and delivery device prior to deployment of the anchor, and/or to determine if repositioning is warranted. More than one sensor may be provided to indicate the spatial extent (e.g., length or surface area) of contact with tissue, the position of the delivery and deployment device and anchor relative to the tissue (positioned to ensure deployment resulting in implantation of the anchor), the degree of purchase of the device with tissue, further information with regard to the implantable device, etc. In some embodiments, multiple sensors can be used, such as to generate various information, such as to indicate both tissue contact as well as the position of the device relative to the tissue. Electronics associated with the sensors can sense resistance, impedance, capacitance, etc. of tissue in contact with the sensors, such as between the sensors (e.g., between electrodes of the sensors). Optimum electrode spacing and the most appropriate sensing method may be determined based on the tissue to which the medical device is to be associated. An optimal system generally will have a maximum signal to noise ratio (SNR), thereby improving sensing confidence. The two primary factors that affect SNR are the sensing method and contact spacing. These values may be determined by experimentation, and it is expected that the optimum configuration is dependent on the target tissue and environment (e.g., ventricle wall and blood field in our case). In some embodiments, the one or more sensors transmit signals generating visual (e.g., an illuminated signal indicating engagement generally, or providing further detailed visual information) and/or audible indicators (e.g., a sound indicating engagement generally, or providing further information), such as on a delivery system or separate associated device. Other forms and manners of providing information with regard to the device, system, method, etc., are within the scope of the present disclosure, the broad concepts not being so limited.

It will be appreciated that the sensors may be formed of conductive materials. Additional conductive components, such as leads, traces, connection pathways, solder pads, wires etc., may be associated with the sensors, such as to convey information to the medical professionals and/or to supply the sensors with power. The conductive materials may be selected from any of a variety of materials such as, without limitation, titanium, niobium, gold, nickel-copper, silver, tin, platinum, palladium, tantalum, tungsten, etc.

In the examples disclosed herein, an anchor delivery and deployment system formed in accordance with various principles of the present disclosure is configured to deliver an anchor disposed within a delivery and deployment device, such as an anchor garage, in a delivery configuration. In some embodiments, the anchor garage is disposed within a catheter, typically with an approximately 0.22 in (5.59 mm) inner diameter, and the anchor garage may have an outer diameter of approximately 0.12 in (3.048 mm) outer diameter (and, in some embodiments, an inner diameter of approximately 0.1065 in/2.7051 mm). For instance, the anchor garage may constrain or hold the anchor talons in a compact configuration to fit within the inner diameter of the anchor garage. In some embodiments, the anchor talons are extended or elongated in the compact configuration to extend along a longitudinal axis of the anchor garage. An actuator, such as a pusher rod, may be used to move the anchor out of the anchor garage for deployment in body tissue. Once the anchor is no longer within the anchor delivery and deployment device, the anchor talons may move into the open configuration, such as an expanded configuration. In the expanded configuration, the anchor may have an outer diameter greater than its outer diameter when in the delivery configuration and greater than the inner diameter of the anchor garage. In accordance with various principles of the present disclosure, sensors are provided on the distal end of the delivery and deployment device, such as the distal end of the anchor garage. An anchor garage with an enlarged or blunt distal end, such as described in the above-referenced incorporated-herein U.S. Provisional Patent Application 63/239,469, filed Sep. 1, 2021, provides sufficient surface area for placement of one or more sensors, such as spaced apart from one another.

As such, various principles of the present disclosure are described herein with reference to embodiments of a tissue anchor, such as for anchoring an artificial chordae tendineae, and associated devices, systems, and mechanisms. However, it will be appreciated that the principles of the present disclosure may be applied more broadly to other devices, systems, methods, etc., configured to engage body tissue. The devices, systems, and methods described herein provide robust solutions for patient safety, particularly with regard to implantable devices. Accordingly, it will be appreciated that devices, systems, and methods described herein may be used with any of the devices, systems, methods, etc., disclosed in the above-referenced applications incorporated herein, or may be used with other devices, systems, methods, etc., such as those described herein or otherwise.

Various embodiments of devices, systems, and methods for positioning an implantable device will now be described with reference to examples illustrated in the accompanying drawings. Reference in this specification to "one embodiment," "an embodiment," "some embodiments", "other embodiments", etc. indicates that one or more particular features, structures, and/or characteristics in accordance with principles of the present disclosure may be included in connection with the embodiment. However, such references do not necessarily mean that all embodiments include the particular features, structures, and/or characteristics, or that an embodiment includes all features, structures, and/or characteristics. Some embodiments may include one or more such features, structures, and/or characteristics, in various combinations thereof. Moreover, references to "one embodiment," "an embodiment," "some embodiments", "other embodiments", etc. in various places in the specification are not necessarily all referring to the same embodiment, nor are separate or alternative embodiments necessarily mutually exclusive of other embodiments. When particular features, structures, and/or characteristics are described in connection with one embodiment, it should be understood that such features, structures, and/or characteristics may also be used in connection with other embodiments whether or not explicitly described, unless clearly stated to the contrary. It should further be understood that such features, structures, and/or characteristics may be used or present singly or in various combinations with one another to create alternative embodiments which are considered part of the present disclosure, as it would be too cumbersome to describe all of the numerous possible combinations and subcombinations of features, structures, and/or characteristics. Moreover, various features, structures, and/or characteristics are described which may be exhibited by some embodiments and not by others. Similarly, various features, structures, and/or characteristics or requirements are described which may be features, structures, and/or characteristics or requirements for some embodiments but may not be features, structures, and/or characteristics or requirements for other embodiments. Therefore, the present disclosure is not limited to only the embodiments specifically described herein.

Turning now to the drawings, it will be appreciated that common features are identified by common reference elements and, for the sake of brevity and convenience, and without intent to limit, the descriptions of the common features are generally not repeated. For purposes of clarity, not all components having the same reference number are numbered.

An example of an embodiment of a system and device to which various principles of the present disclosure may be applied is a delivery and deployment system 100, such as illustrated in FIG. 1. The illustrated example is configured to deliver and to deploy devices for cardiac procedures such as cardiac leaflet repair, although principles of the present disclosure may be applied to other devices delivered transluminally/transcatheterally. The delivery and deployment system 100 includes an anchor delivery and deployment device 110 configured to deliver and to deploy a cardiac anchor 120 with respect to cardiac tissue, as illustrated. Optionally, the delivery and deployment system 100 also includes a leaflet clip spreader 1000 configured to deliver a leaflet clip 1010 (shown more clearly in FIG. 2, with the leaflet clip spreader 1000 in phantom) to a heart leaflet. The delivery and deployment system 100 may be delivered to the deployment site by a delivery catheter 102 which may be guided within a delivery guide sheath 104. The delivery catheter 102 and the delivery guide sheath 104 may be flexible tubular elements (e.g., catheter, sheath, shaft, tube, etc.) steerable through tortuous pathways through the body to allow for transluminal (e.g., transcatheter, in contrast with open surgery) delivery of medical devices within the body, thereby avoiding invasive, open surgery. The delivery guide sheath 104 may be introduced into the body with a dilator through the femoral artery to cross through the septal wall into the ventricle. The delivery catheter 102 may be steerable (such as formed with articulations) to be positioned substantially centered above the mitral valve. The anchor delivery and deployment device 110 may be carried by a shaft 106 extendable out of the delivery catheter 102 or retractable into the delivery catheter 102 (e.g., telescoping in or out of the delivery catheter 102) to be brought into position relative (e.g., closer) to a treatment site in the heart.

In accordance with various principles of the present disclosure, the anchor delivery and deployment device 110 is configured to house or to hold an implantable device, such as an anchor 120. The implantable device may be shiftable from such delivery configuration to a deployment configuration. The delivery configuration of the implantable device may be a generally unexpanded configuration, and the deployment configuration of the implantable device may be a generally expanded configuration. The anchor delivery and deployment device 110 may be configured to deliver the implantable device in a delivery configuration, as may be appreciated with reference to FIG. 2 and FIG. 3. In the illustrated example of an embodiment, the anchor delivery and deployment device 110 includes a delivery device configured to carry or hold an implantable device during delivery of the implantable device, and may be in the form of, without limitation, the distal end of a delivery shaft 108 or an anchor garage 130 (which may be operatively associated with the end of the delivery shaft 108, as may be seen in FIG. 2). For the sake of convenience, and without intent to limit, reference is made herein to the anchor garage 130, such reference being understood to include other configurations of delivery devices than the illustrated anchor garage 130. The anchor garage 130 may be configured with an open blunt distal end 131 (tip or free end) sized, shaped, configured, and dimensioned to facilitate pushing of the anchor garage 130 against cardiac tissue to deploy the anchor 120 out of the anchor garage 130 and into tissue T at the deployment site without potentially pushing the distal end 131 of the anchor garage 130 into the cardiac tissue as well.

For instance, the distal end 131 of the anchor garage 130 may be radiused or curved inwardly (presenting a convex curved outer surface) or otherwise formed to be sufficiently blunt as to not injure tissue against which the anchor garage 130 is pushed. For example, and without limitation, edges of the distal end 131 of the anchor garage 130 may curved with a radius of approximately 0.0275" (0.6985 mm).

Figure 2:
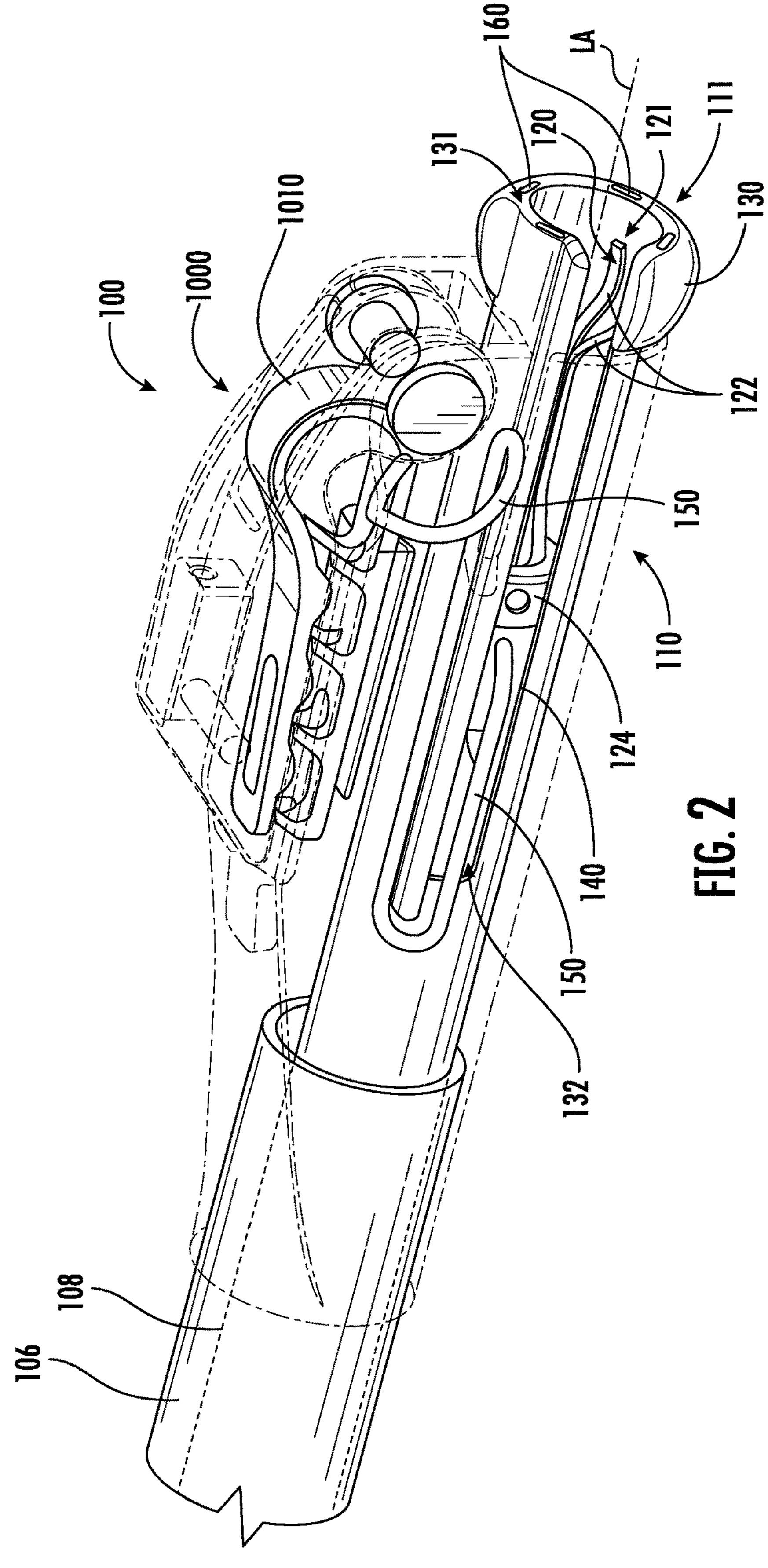
FIG. 2 illustrates a perspective view of an example of an embodiment of an anchor delivery and deployment device and system formed in accordance with various principles of the present disclosure, and with a delivery catheter and leaflet clip delivery/deployment system optionally associated therewith illustrated in phantom.
Figure 3:
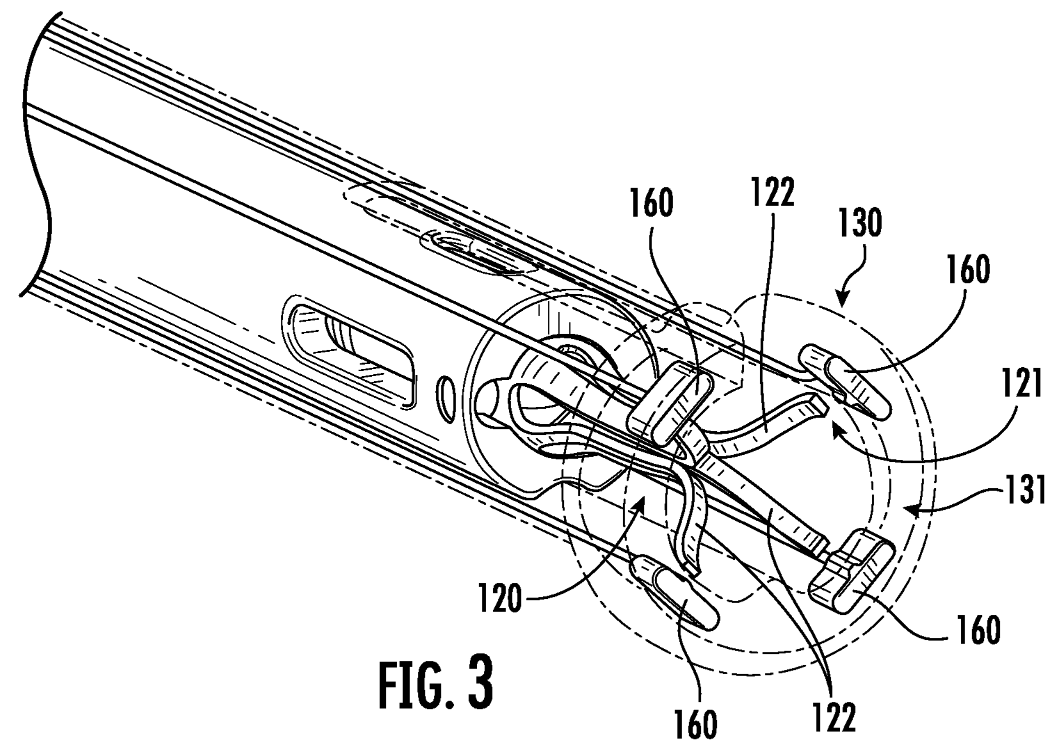
FIG. 3 illustrates a further perspective view of an example of an embodiment of an anchor delivery and deployment device and system such as illustrated in FIG. 2, further illustrating examples of embodiments of sensors positioned at a distal end of the anchor delivery and deployment device and system in accordance with various principles of the present disclosure.

As may be appreciated with reference to FIG. 2 and FIG. 3, an anchor 120 formed in accordance with various principles of the present disclosure has a plurality of talons 122 extending distally, such as from an anchor body 124, to distal ends 121 thereof. The anchor 120 may be coupled with an artificial chordae tendineae tensioning and locking device 140 to anchor an artificial chordae tendineae 150 with the anchor 120. The artificial chordae tendineae tensioning and locking device 140 is structured and configured to receive an artificial chordae tendineae 150 and to hold the artificial chordae tendineae 150 in a desired position and/or configuration, such as with respect to the anchor 120. The specific structure of the artificial chordae tendineae tensioning and locking device 140 is not critical to the present disclosure and may be any desired structure, including, but not limited to, structures disclosed in any of the patent applications referenced and/or incorporated by reference herein.

It is generally desirable for an anchor 120 used with devices, systems, and methods of the present disclosure to establish a strong purchase in or with the tissue so that the anchor 120 is not inadvertently withdrawn from the tissue. The anchor 120 thus may be dimensioned, shaped, formed, and configured to resist tension exerted thereon (such as by movement of a leaflet to which the artificial chordae tendineae 150 coupled to the anchor 120 is also coupled). The distal ends 121 of the anchor talons 122 may each have a tapered or pointed tip suitable for piercing tissue so that the talons 122 may penetrate into tissue so that the anchor 120 may be securely fixed to tissue when the anchor 120 is engaged therewith. The talons 122 may be curved or bowed or otherwise configured to move the distal ends 121 thereof in a direction which secures the anchor to tissue. For instance, the talons 122 may shift radially outwardly away from the longitudinal axis LA of the anchor delivery and deployment system 100, such as to bend back towards the anchor body 124, when the anchor 120 is moved from a delivery configuration (e.g., within the anchor garage 130, such as illustrated in FIG. 3) to a deployed configuration (e.g., outside the anchor garage 130), such as within the tissue T at the deployment site. It will be appreciated that other movements or bending or otherwise of the talons 122 to secure purchase of the anchor 120 within tissue T at the deployment site (such as by moving radially inwardly or outwardly to be transverse to the longitudinal axis of the anchor 120) are within the scope of the present disclosure. In some embodiments, the talons 122 may be formed of shape memory material, and, optionally, act as a spring to shift the distal ends 121 into a deployed configuration. In embodiments in which the anchor is anchored in heart tissue (such as to anchor an artificial chordae tendineae to papillary muscle), the strength of the talons generally must be balanced with the flexibility of the talons. For instance, the talons should be sufficiently strong to endure multiple palpatory forces thereon (e.g., over 800 million cycles), yet not to deform or break upon changing shape (e.g., bending or straightening, such as when shifting between the delivery and deployed configurations). The thickness (in a radial direction) of at least some of the talons may be modified to achieve the desired pull out resistance/purchase strength in tissue (thicker talons generally are stronger with a greater holding force) while not being so thick as to potentially deform or break. Additionally or alternatively, the width of the talons may be selected to achieve the desired tissue purchase strength as well as material strength (to resist deforming or breaking). The length of the talons formed therefrom may be selected so that the talons penetrate sufficiently into tissue, yet are not so long so that the distal ends thereof exit the tissue (e.g., enter from one side and exit from another side, or enter and bend through the tissue and exit from the same side of the tissue as the point of entry). Various further details of the shapes and configurations of the anchor 120 and the talons 122 may be appreciated by those of ordinary skill in the art, the present disclosure not being limited by such details.

It will be appreciated that if an anchor 120 with talons 122 pre-shaped to move upon deployment from an anchor delivery and deployment device 110, such as described above, is deployed without the distal ends 121 thereof engaging with the tissue in which the anchor 120 is to be implanted, the talons 122 may move into a deployed configuration without having penetrated the tissue. To ensure proper deployment of an anchor 120 as described above, it is generally important for the distal ends 121 of the talons 122 thereof to contact tissue prior to deployment of the anchor 120 and movement of the talons 122 into a deployed configuration. Additionally, it is desirable to ensure that the anchor 120 is deployed in the appropriate position and/or type of tissue so that the anchor 120 is securely engaged with the tissue for the desired purpose (e.g., to anchor an artificial chordae tendineae 150 to papillary muscle tissue).

In accordance with various principles of the present disclosure, to facilitate deployment of an anchor 120 to ensure secure engagement with tissue (e.g., to secure another implantable device, such as an artificial chordae tendineae 150, to the tissue), and/or to facilitate proper placement of the anchor 120, one or more sensors 160 are associated with the anchor delivery and deployment device 110 such as to be associated with the anchor 120. For instance the one or more sensors 160 may be associated with the anchor garage 130 and thereby associated with the anchor 120. More particularly, the sensors 160 may be positioned spaced apart along a distal end 101 of the anchor delivery and deployment device 110, such as on a distal end 131 of the anchor garage 130 and spaced apart along a perimeter thereof. As noted above, the distal end 131 of the anchor garage 130 may be a blunt radiused end, and may be sized, shaped, configured, and dimensioned in a manner understood by those of ordinary skill in the art to provide sufficient space for the sensors 160 to be positioned to effectively contact tissue to generate the desired signal upon contact with tissue. For instance, the distal end 131 of the anchor garage 130 may have an outer diameter of approximately 0.175" (4.445 mm) and an inner diameter of approximately 0.107" (2.718 mm), with an electrode size approximately 0.015" (0.381 mm)×0.030" (0.762 mm). In some embodiments, the one or more sensors 160 may be positioned immediately adjacent a respective talon 122 of an anchor 120 to indicate contact of the anchor garage 130 with tissue. Contact of the anchor garage 130 with tissue should guarantee the desired intimate contact of the talons 122 with tissue at the time of deployment of the anchor 120 to ensure purchase of the tissue by the talons 122. Various suitable sensors are available to generate useful and usable signals indicating whether the anchor delivery and deployment device 110 is in contact with tissue or is otherwise ready for deployment of an anchor. For instance, the sensors 160 may be contact sensors (e.g., including electrodes generating a signal upon contact with tissue)

and/or impedance sensors (measuring impedance of the material being contacted by the sensor) capable of indicating that the anchor delivery and deployment device 110 is in contact with tissue so that engagement of the talons 122 of the anchor 120 may be ensured. In some embodiments, the sensors 160 may sense various parameters, such as impedance resistance, impedance, capacitance, etc., between one another to indicate contact, position, type of tissue contacted (e.g., fat tissue vs. muscle tissue), and other information useful for proper/desired deployment of the anchor 120.

Figure 4:
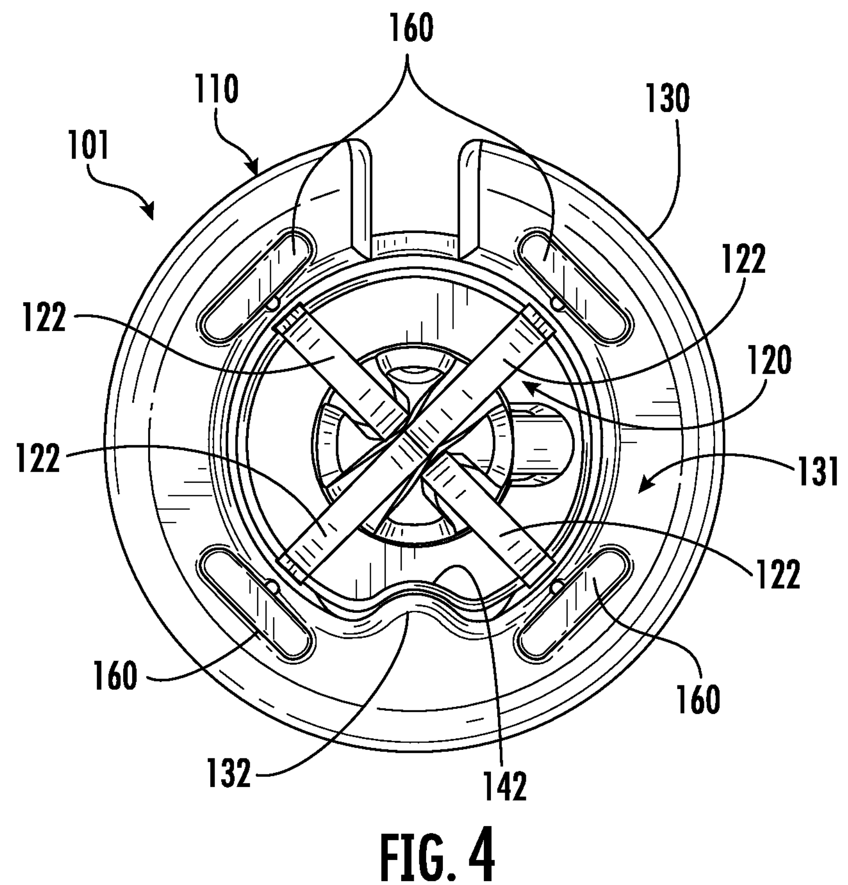
FIG. 4 is an end view of an anchor delivery and deployment device as in FIG. 3.

In accordance with various principles of the present disclosure, at least three sensors 160 are provided along a distal end 111 of the anchor delivery and deployment device 110, such as illustrated in FIG. 2, FIG. 3, and FIG. 4. The at least three sensors 160 define a plane along the distal end 111 of the anchor delivery and deployment device 110 such that if all three sensors 160 are in contact with tissue, then the plane in which the distal end 111 of the anchor delivery and deployment device 110 lies is in contact with tissue, and the talons 122 of the anchor 120 (delivered by the anchor delivery and deployment device 110) should contact tissue upon deployment from the anchor delivery and deployment device 110. In other words, when all sensors 160 on the distal end 111 of the anchor delivery and deployment device 110 are in contact with tissue, the distal end 111 should be "square" against the tissue (e.g., fully in contact with the tissue around the perimeter of the delivery and deployment device 110) and not at an angle. Confirmation of such position should guarantee that all talons 122 of the anchor 120 will engage tissue upon deployment and achieve the desired penetration and purchase of the tissue. If the anchor delivery and deployment device 110 is at an angle, then some of the talons 122 likely will not purchase the tissue T at the treatment site. It will be appreciated that more than three sensors 160 may be provided.

In some embodiments, each talon 122 of the anchor 120 to be deployed may have an associated sensor 160 provided adjacent and/or aligned therewith. In the example of an embodiment illustrated in FIG. 2, FIG. 3, and FIG. 4, four sensors 160 are provided, each aligned with a talon 122 of the anchor 120. At least a portion of the anchor 120 and at least a portion of the anchor delivery and deployment device 110 may be provided with corresponding clocking features to maintain alignment of the anchor 120 with respect to the sensors 160 on the anchor delivery and deployment device 110, or otherwise to hold the anchor 120 in place or otherwise maintained in a selected position with respect to the delivery and deployment device 110. In some embodiments, the clocking features include a groove or projection on a portion of the anchor 120 and a corresponding mating projection or groove on the anchor delivery and deployment device 110. In some embodiments, as illustrated in FIG. 4, a clocking feature 142 (such as in the form of a longitudinally-extending groove) may be provided or formed on a body of the anchor and/or on an artificial chordae tendineae tensioning and locking device 140 associated or coupled with the anchor 120, and a corresponding clocking feature 132 (such in the form of a longitudinally-extending projection or rib) may be provided or formed on an anchor garage 130 in which the anchor 120 is delivered to a deployment site. Engagement of the clocking features 142, 132 inhibits relative rotation of the anchor 120 and its associated talons 122 with respect to the anchor delivery and deployment device 110 and its associated sensors 160. In some embodiments, the clocking features 142, 132 may also align an artificial chordae tendineae 150 extending from the anchor 120 (such as from an artificial chordae tendineae tensioning and locking device 140) with a slot 132 in the anchor garage 130 to extend to a leaflet clip 1010. In some embodiments, the anchor garage 130 may be formed of metal or polymer, and is bonded over a delivery catheter or shaft 108 (illustrated in phantom in FIG. 2) generally formed of a polymer (but which may optionally be formed of a combination of polymer and a metal braid or coil, or a metal). The anchor garage 130 and the artificial chordae tendineae tensioning and locking device 140 may be machined or molded or otherwise formed in a manner known to those of ordinary skill in the art to include clocking features 142, 132 (such as, without limitation, those described above).

Sensors 160 may be formed in any desired manner to sense contact with tissue and to generate an appropriate signal indicating contact with tissue. For instance, the sensors 160 are configured to sense and generate a signal (e.g., an impedance measurement), and thus generally are electrically conductive. Various suitable sensors such as known to those of ordinary skill in the art are available to generate useful and usable signals indicating whether the anchor delivery and deployment device 110 and the anchor 130 are in position or in contact or otherwise ready for deployment of the anchor 120. In accordance with various principles of the present disclosure, three or more sensors 160 are provided which can indicate contact with tissue. In some embodiments, a signal is generated when all three sensors 160 contact tissue. In some embodiments, a signal is generated for each of the sensors 160 separately (such as to indicate an angular position of anchor delivery and deployment device 110 with respect to the tissue T at the treatment site). Such information may be used by the medical professional to adjust the position of the anchor delivery and deployment device 110 as necessary to ensure proper delivery and deployment of the anchor 120. One or more of the three or more sensors 160 optionally may identify the type of tissue being contacted. For instance, the sensor may be a contact sensor as well as an impedance sensor which measures impedance of the material being contacted by the sensor. Such impedance-based sensors may be used in technology used in electrophysiology devices which map the heart, such as based on electrical activity of the heart to distinguish body tissue from other materials and/or to distinguish different types of tissue (e.g., muscle, fat, etc.) based on the impedance measured upon contact with such tissue. The sensors 160 may be formed of a conductive, biocompatible material, such as, without limitation, niobium, silver, titanium, tungsten, tantalum, etc., as well as nitrides or oxides. Selection of the material of the conductive layer 146 may be influenced by the desired sensing function (e.g., impedance measuring capacity), associated circuitry, electrical requirements, signal output requirements, etc.

In some embodiments, the sensors 160 are formed as a flexible circuit board with one or more contacts (e.g., exposed pads or other contact features). For instance, the circuit board may include a metallized plate with various areas insulated relative to each other, and conductive sensors which generate a signal upon contact with tissue. The circuit board may be generally insulative except at the exposed pads or other contact features of the sensors. Insulated wires, such as known in the art for delivering power to the circuit board and for transmitting signals from the sensor to a device to indicate information to the medical professional (such as contact of the sensors 160 with tissue), etc., may pass through holes in the circuit board and proximally through or along the various catheters/shafts 108, 106, 104, 102 of the delivery/deployment system 100. Alternatively, the sensors may be individual pads, such as provided with insulative material to insulate the pads from the anchor garage 130 or other conductive elements. The sensors 160 may be stamped, machined, printed, or formed on a substrate in any desired manner including, without limitation, adhesion, interference fit (e.g., fitting in a groove, pocket, recess, etc.), physical vapor deposition (e.g., sputter-coating, thermal evaporation, arc spraying, etc.), electroless plating, electrolytic plating, brazing, or other bonding method. Regions of the anchor delivery and deployment device 110 on which the sensors 160 are provided (e.g., an anchor garage 130) may be masked or otherwise protected to limit the area to which the material of the sensors 160 and/or any associated leads, traces, connection pathways, solder pads, etc., are applied. Other configurations of sensors 160 are within the scope of the present disclosure, the details not being critical to the principles of the present disclosure.

As indicated above, in order to transmit information sensed by the one or more sensors 160 to the medical professional navigating the delivery and deployment system 100, and/or to transmit power to the one or more sensors 160, at least one lead wire extends from at least one sensor 160 proximally along the delivery and deployment system 100 to a proximal location at which power may be supplied to the lead wire and/or the lead wire may be coupled to an indicator which generates a signal from the one or more sensors 160. As may be appreciated, the indicator may be any known indicator configured to provide the desired information in a desired format or configuration to the medical professional operating the delivery and deployment system 100. For instance, the signal may simply be a red light indicating insufficient or no contact, or a green light indicating sufficient or complete contact. Further detailed signals, such as to provide more detailed information with regard to the position, location, degree of purchase or engagement, etc., of the anchor 120 (or another implantable device) may be generated, the details of which are not critical to the broad principles of the present disclosure. Each sensor 140 may have its own lead wire. Because of the generally limited wall thickness of the anchor delivery and deployment device 110 (e.g., the anchor garage 130), the lead wires of the sensors 160 may extend together along a common passage in the anchor garage 130 to extend into the delivery shaft 108 to extend proximally to a station (such as for power, or a signal indicator device). In some embodiments, the common channel is formed within a clocking feature 132 in the form of an axial projection along the anchor garage 130, such projection providing the added wall thickness to accommodate the lead wires As may be appreciated by one of ordinary skill in the art, it may be challenging to achieve proper purchase of tissue with various implantable devices, such as devices with shape memory components which flex or bend upon deployment, such as the talons of a tissue anchor. The provision of one or more sensors as disclosed herein allows for confirmation of the desired engagement, placement, purchase, etc., of tissue by the implantable device. Signals generated by the sensors advantageously may thus facilitate accurate and efficient placement and deployment of an anchor into heart tissue such as to anchor an artificial chordae tendineae thereto to repair a valve leaflet. Although embodiments of the present disclosure may be described with specific reference to a tissue anchor, such as for implanting into a heart (and, more particularly, for anchoring an artificial chordae tendineae to cardiac tissue), it will be appreciated that various other implantable devices may benefit from the devices, systems, and methods described herein. For example, other implantable devices for use with the heart and which must withstand the palpatory forces of the heart (e.g., implantable devices for use with/repairing heart such as mitral valves or tricuspid valves and/or addressing other dilatation, valve incompetency, valve leakage, and other similar heart failure conditions) may also benefit from the concepts disclosed herein. Furthermore, it will be appreciated that the broad principles and concepts described above with respect to the heart are applicable to other delivery/deployment systems for other types of devices delivered and/or deployed to other locations within a body.

It should be understood that, as described herein, an "embodiment" (such as illustrated in the accompanying Figures) may refer to an illustrative representation of an environment or article or component in which a disclosed concept or feature may be provided or embodied, or to the representation of a manner in which just the concept or feature may be provided or embodied. However such illustrated embodiments are to be understood as examples (unless otherwise stated), and other manners of embodying the described concepts or features, such as may be understood by one of ordinary skill in the art upon learning the concepts or features from the present disclosure, are within the scope of the disclosure. In addition, it will be appreciated that while the Figures may show one or more embodiments of concepts or features together in a single embodiment of an environment, article, or component incorporating such concepts or features, such concepts or features are to be understood (unless otherwise specified) as independent of and separate from one another and are shown together for the sake of convenience and without intent to limit to being present or used together. For instance, features illustrated or described as part of one embodiment can be used separately, or with one or more other features to yield a still further embodiment. Thus, it is intended that the present subject matter covers such modifications and variations as come within the scope of the appended claims and their equivalents.

The foregoing discussion has broad application and has been presented for purposes of illustration and description and is not intended to limit the disclosure to the form or forms disclosed herein. It will be understood that various additions, modifications, and substitutions may be made to embodiments disclosed herein without departing from the concept, spirit, and scope of the present disclosure. In particular, it will be clear to those skilled in the art that principles of the present disclosure may be embodied in other forms, structures, arrangements, proportions, and with other elements, materials, and components, without departing from the concept, spirit, or scope, or characteristics thereof. For example, various features of the disclosure are grouped together in one or more aspects, embodiments, or configurations for the purpose of streamlining the disclosure. However, it should be understood that various features of the certain aspects, embodiments, or configurations of the disclosure may be combined in alternate aspects, embodiments, or configurations. While the disclosure is presented in terms of embodiments, it should be appreciated that the various separate features of the present subject matter need not all be present in order to achieve at least some of the desired characteristics and/or benefits of the present subject matter or such individual features. One skilled in the art will appreciate that the disclosure may be used with many modifications or modifications of structure, arrangement, proportions, materials, components, and otherwise, used in the practice of the disclosure, which are particularly adapted to specific environments and operative requirements without departing from the principles or spirit or scope of the present disclosure. For example, elements shown as integrally formed may be constructed of multiple parts or elements shown as multiple parts may be integrally formed, the operation of elements may be reversed or otherwise varied, the size or dimensions of the elements may be varied. Similarly, while operations or actions or procedures are described in a particular order, this should not be understood as requiring such particular order, or that all operations or actions or procedures are to be performed, to achieve desirable results. Additionally, other implementations are within the scope of the following claims. In some cases, the actions recited in the claims can be performed in a different order and still achieve desirable results. The presently disclosed embodiments are therefore to be considered in all respects as illustrative and not restrictive, the scope of the claimed subject matter being indicated by the appended claims, and not limited to the foregoing description or particular embodiments or arrangements described or illustrated herein. In view of the foregoing, individual features of any embodiment may be used and can be claimed separately or in combination with features of that embodiment or any other embodiment, the scope of the subject matter being indicated by the appended claims, and not limited to the foregoing description.

In the foregoing description and the following claims, the following will be appreciated. The phrases "at least one", "one or more", and "and/or", as used herein, are open-ended expressions that are both conjunctive and disjunctive in operation. The terms "a", "an", "the", "first", "second", etc., do not preclude a plurality. For example, the term "a" or "an" entity, as used herein, refers to one or more of that entity. As such, the terms "a" (or "an"), "one or more" and "at least one" can be used interchangeably herein. All directional references (e.g., proximal, distal, upper, lower, upward, downward, left, right, lateral, longitudinal, front, back, top, bottom, above, below, vertical, horizontal, radial, axial, clockwise, counterclockwise, and/or the like) are only used for identification purposes to aid the reader's understanding of the present disclosure, and/or serve to distinguish regions of the associated elements from one another, and do not limit the associated element, particularly as to the position, orientation, or use of this disclosure. Connection references (e.g., attached, coupled, connected, and joined) are to be construed broadly and may include intermediate members between a collection of elements and relative movement between elements unless otherwise indicated. As such, connection references do not necessarily infer that two elements are directly connected and in fixed relation to each other. Identification references (e.g., primary, secondary, first, second, third, fourth, etc.) are not intended to connote importance or priority, but are used to distinguish one feature from another.

The following claims are hereby incorporated into this Detailed Description by this reference, with each claim standing on its own as a separate embodiment of the present disclosure. In the claims, the term "comprises/comprising" does not exclude the presence of other elements, components, features, regions, integers, steps, operations, etc. Additionally, although individual features may be included in different claims, these may possibly advantageously be combined, and the inclusion in different claims does not imply that a combination of features is not feasible and/or advantageous. In addition, singular references do not exclude a plurality. Reference signs in the claims are provided merely as a clarifying example and shall not be construed as limiting the scope of the claims in any way.

What is claimed is:

1. A delivery and deployment device for transluminally delivering and/or deploying an implantable device at a deployment site within a body, the implantable device having a portion which shifts from a delivery configuration to a deployment configuration upon deployment, the delivery and deployment device comprising:

a delivery device configured to deliver an implantable device;

wherein the delivery device comprises an anchor garage configured to deliver a tissue anchor to a deployment site, the tissue anchor having two or more talons shiftable from a delivery configuration to a deployment configuration; and three or more sensors positioned along a distal end of the delivery device and configured to generate a signal when the distal end of the delivery device is in contact with tissue to ensure purchase of tissue by the implantable device upon deployment.

2. The delivery and deployment device of claim 1, wherein the three or more sensors are positioned spaced apart along a periphery of a distal end of the delivery device.

3. The delivery and deployment device of claim 2, wherein the three or more sensors are equidistantly spaced apart from one another.

4. The delivery and deployment device of claim 1, wherein the three or more sensors include at least one sensor associated with each talon of the tissue anchor delivered by the anchor garage.

5. The delivery and deployment device of claim 1, wherein the anchor garage has a blunt distal end along which the three or more sensors are positioned.

6. The delivery and deployment device of claim 1, wherein the three or more sensors include contact sensors.

7. The delivery and deployment device of claim 1, further comprising a delivery shaft through which lead wires extend from the three or more sensors.

8. A system for delivering and deploying an implantable device to a deployment site in a body, the system comprising:

an implantable device;

a delivery device configured to deliver the implantable device to the deployment site;

wherein the delivery device comprises an anchor garage configured to deliver a tissue anchor to a deployment site, the tissue anchor having two or more talons shiftable from a delivery configuration to a deployment configuration; and three or more sensors positioned along a distal end of the delivery device and configured to generate a signal when the distal end of the delivery device is in contact with tissue to ensure purchase of tissue by the implantable device upon deployment without the need for imaging.

9. The system of claim 8, wherein the three or more sensors are positioned spaced apart along a periphery of a distal end of the delivery device.

10. The delivery and deployment system of claim 8, wherein:

the implantable device is a tissue anchor; and the anchor garage is configured to deliver the tissue anchor to a deployment site.

11. The system of claim 10, wherein the tissue anchor is clocked with respect to the anchor garage.

12. The system of claim 11, wherein:

the tissue anchor has two or more talons shiftable from a delivery configuration to a deployment configuration; and the three or more sensors include at least one sensor associated with a talon of the tissue anchor.

13. The system of claim 11, wherein the anchor garage includes a projection extending longitudinally along a portion thereof engaging a groove extending longitudinally along a portion of the tissue anchor to clock the tissue anchor with respect to the anchor garage.

14. The system of claim 13, wherein lead wires from the three or more sensors extend within the projection along the anchor garage to a device generating a signal indicating contact of the three or more sensors with tissue.

15. The system of claim 11, wherein the tissue anchor is clocked with respect to the anchor garage to align at least one of the talons of the tissue anchor with a sensor of the three or more sensors.

16. The system of claim 11, further comprising an artificial chordae tendineae tensioning and locking device associated with the tissue anchor, wherein the tissue anchor is clocked with respect to the anchor garage to align an artificial chordae tendineae associated with the artificial chordae tendineae tensioning and locking device with a groove in the anchor garage.

17. A method of delivering and deploying an implantable device, the method comprising:

delivering a delivery and deployment device transluminally to a deployment site within a body;

wherein the delivery and deployment device comprises an anchor garage configured to deliver a tissue anchor to a deployment site, the tissue anchor having two or more talons shiftable from a delivery configuration to a deployment configuration; and contacting three or more sensors on a distal end of the delivery and deployment device with tissue at the delivery site to generate a signal indicative of a position of the delivery and deployment device ensuring purchase of the implantable device with tissue at the deployment site.

18. The method of claim 17, wherein the three or more sensors are positioned spaced apart along a distal end of the delivery and deployment device, the method further comprising deploying the implantable device when three of the three or more sensors generate a signal indicating contact with tissue.

19. The method of claim 18, wherein the deployment site is cardiac tissue and the implantable device is a tissue anchor, the method further comprising deploying the tissue anchor into cardiac tissue when all three of the three or more sensors generate a signal indicating contact of a distal end of the delivery and deployment device with tissue at the deployment site and without imaging the implantable device or the deployment site.

* * * * *